US008560349B2

(12) United States Patent
Coe

(10) Patent No.: US 8,560,349 B2
(45) Date of Patent: Oct. 15, 2013

(54) METHOD OF DOCUMENTING ANIMAL TREATMENT

(75) Inventor: Michael Coe, Summit, NJ (US)

(73) Assignees: Intervet Inc., Summit, NJ (US); Intervet International B.V., Boxmeer (NL)

( * ) Notice: Subject to any disclaimer, the term of this patent is extended or adjusted under 35 U.S.C. 154(b) by 162 days.

(21) Appl. No.: 13/125,021

(22) PCT Filed: Oct. 20, 2009

(86) PCT No.: PCT/US2009/061259
§ 371 (c)(1),
(2), (4) Date: Apr. 19, 2011

(87) PCT Pub. No.: WO2010/048136
PCT Pub. Date: Apr. 29, 2010

(65) Prior Publication Data
US 2011/0202577 A1 Aug. 18, 2011

Related U.S. Application Data

(60) Provisional application No. 61/107,389, filed on Oct. 22, 2008.

(51) Int. Cl.
*G06F 19/00* (2011.01)
(52) U.S. Cl.
USPC .......................................................... 705/3
(58) Field of Classification Search
USPC ......... 705/2, 3, 75; 700/79; 702/19; 717/124; 395/600; 379/113
See application file for complete search history.

(56) References Cited

U.S. PATENT DOCUMENTS

| 5,446,880 | A | * | 8/1995 | Balgeman et al. | 1/1 |
| 6,002,753 | A | * | 12/1999 | Morrison et al. | 379/112.01 |
| 2002/0069086 | A1 | * | 6/2002 | Fracek et al. | 705/2 |
| 2002/0072991 | A1 | * | 6/2002 | Kane | 705/26 |
| 2003/0153991 | A1 | * | 8/2003 | Visser et al. | 700/79 |
| 2003/0229452 | A1 | * | 12/2003 | Lewis et al. | 702/19 |
| 2006/0117301 | A1 | * | 6/2006 | Saunders et al. | 717/124 |

OTHER PUBLICATIONS

"NAIS—A User Guide and Additional Information Resources"; Version 2.0; Dec. 2007; USDA.*
"Notice from the European Patent Office Dated Oct. 1, 2007 Concerning Business Methods", Official Journal of the European Patent Office, vol. 30, No. 11, Nov. 1, 2007, pp. 592-593.
"Statement in Accordance with the Notice from the European Patent Office Dated Oct. 1, 2007 Concerning Business Methods—PCT", Official Journal of the European Patent Office, Nov. 1, 2007, pp. 592-593.
International Search Report in corresponding PCT/US2009/061259, mailed Dec. 9, 2009.

* cited by examiner

*Primary Examiner* — John Pauls

(57) ABSTRACT

A method of documenting animal treatment, comprising the steps of: —downloading an electronic report form from a server via a network; —when an animal is treated, entering information on the treatment into the report form, said information identifying the type of treatment and including at least a unique identifier of the treatment act; and—starting a software program that automatically sends data that have been entered into the report form to a plurality of remote databases via the network and causes the data to be entered into the databases and further controls a writer to write a copy of the report, which copy is a certificate that proves sending of the data to the databases.

15 Claims, 3 Drawing Sheets

Fig. 3

METHOD OF DOCUMENTING ANIMAL TREATMENT

CROSS-REFERENCE TO RELATED APPLICATIONS

This application is a national stage entry under 35 U.S.C. §371 of PCT/US2009/061259 filed on Oct. 20, 2009, which claims priority to U.S. Application No. 61/107,389 filed on Oct. 22, 2008, the contents of which are hereby incorporated by reference in their entireties.

BACKGROUND OF THE INVENTION

The invention relates to a method of documenting animal treatment. More particularly, the invention relates to a method of documenting vaccination treatment against Governmentally Regulated Diseases.

In many countries of the world, governments have established regulations and monitoring systems for dealing with specific types of animal diseases, the so called Governmentally Regulated Diseases, especially emerging diseases, which bear a high risk for man and animal, such as brucellosis, scrapie, blue tongue, pseudo rabies, chronic waste disease, Johne's disease, equine infectious anemia, avian influenza, and the like.

For example, in the United States, Federal and State legislation require not only that calves are vaccinated again brucellosis, but require also that the vaccinations are certified by an accredited veterinarian and are reported to Federal and State authorities. To that end, the authorities provide printed report forms which are filled-in by the veterinarian when he vaccinates the animals of a herd of a farmer. Further, the veterinarian applies a specific tag to an ear of the animal. These tags are administrated by a Federal authority (USDA) and each bear a unique identifier, i.e. a unique number that will then also be entered into the report form along with a description of the animal that has be tagged and vaccinated. Then, separate copies of the completed form are sent to the Federal authorities and the State authorities, and another copy is kept in the file of the veterinarian or the herd owner and will serve as a vaccination certificate.

Similar reporting schemes exist also in other countries. In general, it can be said that regional and national authorities and even supranational authorities tend to establish and improve systems which permit to combat harmful emerging animal diseases more effectively. Moreover, these authorities are increasingly co-operating with commercial companies and institutions that are involved in stock breeding. In this context, many companies and institutions favor the introduction of event based database systems which permit to trace individual animals and animal products throughout the distribution chain and to comprehensively document all important events in animal life such as birth, tagging, vaccination, curative treatment, transport, use for breeding, disease, death by disease, slaughter, disappearance and like some of these events may be governmentally regulated), with the intention to aid prevention of diseases and to give powerful support in case of an outbreak.

in the US, for example, the National Animal Identification System (WAIS) has resulted in the development of the National Premises Information Management System and the Animal Trace Process System (ATPS), which involve the development of event based Animal Tracking Databases (ATD's).

These attempts to establish an efficient and networked disease management structure depend crucially on diligent and continual cooperation of all entities involved, especially stock breeders and veterinarians. On this background, the conventional paper-based reporting systems become increasingly problematic because they are prone to errors and failures and imply and increasing workload on veterinarians and/or animal owners. Especially, with an increasing number of database systems for an increasing number of diseases, it becomes more and more difficult for individuals to keep an oversight over which information has to be reported to which authority or institution.

SUMMARY OF THE INVENTION

It is therefore an object of the invention to provide a method of documenting animal treatment that is easy to handle and more reliable.

In order to achieve this object, the method according to the invention comprises the steps of:

downloading an electronic report form from a server via a network;

when an animal is treated, entering information on the treatment into the report form, said information identifying the type of treatment and including at least a unique identifier of the treatment act; and starting a software program that automatically sends data that have been entered into the report form to a plurality of remote databases via the network and causes the data to be entered into the databases and further causes a writer to write a copy of the report which copy is a certificate that proves sending of the data to the databases.

In the method according to the invention a plurality of databases to which information has to be reported are specified in the software program that attends to automatically sending the pertinent data to the respective databases and attends also to the writing of a copy of the report, which serves as a certificate for sending the data and inherently also for the fact that the treatment took place. Such a writer may for example be a common printer which prints a hard copy of the report, which hard copy may be regarded as a certificate. However, in an other embodiment the writer is a unit that writes a digital certification copy, preferably a read-only copy, in a digital memory, for example a CD, DVD, hard-disk, magnetic tape, USB-device etc. This memory preferably is protected against unlawful or other unwanted entry. In any case, whenever a certificate copy of the report has been written, it can be taken for granted that the databases of all pertinent authorities and institutions have received the data they ask for. The certificate printing preferably takes place via a secure internet-line, and may be initiated as soon as it is verified that the data is at least received by the various databases. Actual entry in the definitive database may take place at a later stage, for example only after additional checks have been performed.

The layout of the electronic report form may image the layout of existing report forms on paper sheets which individuals today are used to work with. Since the report form according to the invention is downloaded (i.e. made locally available, e.g. at a workstation, PC, handheld, laptop etc.) from a server (i.e. a central unit that provides the requested service), modifications and additions to the report form may easily be implemented, and it is assured that the forms that are used by the veterinarians, for example, are always are up to date. Moreover, since the process of extracting the relevant information from the report form and sending it to the specified databases is automated, many sources of transcription and transmission errors are eliminated.

Moreover, once the report form is available in an electronic format that is suitable for data processing, it is easy to implement several checks for automatically detecting errors (e.g. wrong premises number, wrong identifiers) and/or inconsistencies (e.g. the identifier is inconsistent with the type of treatment) once the form has been filled-in. When these checks have been passed, the work of sending the report to the various authorities reduces to a single mouse click for starting the software program that will attend to the further distribution of the information and the writing of the certification copy.

It will also be appreciated that the method according to the invention is flexible and facilitates the integration of more sophisticated future monitoring systems.

Useful further developments of the invention are indicated in the dependent claims.

Preferably, the databases that are specified in the software program and to which the data from the report form are to be sent, include at least one event based database such as an animal tracking database. Since the reports to the various databases, including the event based database, and the writing of a certificate copy are integrated into a single inseparable action (which action may be divided in multiple sub-actions), the invention facilitates maintenance and updating of the event based database without additional workload and promotes the spreading of event based database and animal tracking systems. When it has become common practice that each new born animal has a record in such an invent based database, government authorities may exchange data with this database and, accordingly, will have access not only to records showing that an animal has been vaccinated but also to records showing animals for which vaccination regulations have not yet been complied with.

When an animal is treated, it may at the same time be tagged with an ear tag in the usual way, and the minimum information to be included in the electronic report, i.e. the type of treatment and the unique; identifier should also be encoded on the tag.

As an alternative to or in addition to tagging, any other suitable marking techniques such as tattoos and the like may be used.

In general, different tags (or marks) may be provided for different types of treatment, e.g. for vaccinations against different diseases. In that case, each tag will bear a unique tag identifier which will then be entered into the electronic report form. One of these tag identifiers, for a specific type of disease, may simultaneously have the function of an animal identifier. As an alternative, an animal identifier may be assigned to each animal independently of the various tag identifiers.

In a particularly preferred embodiment, the information is encoded on the tag in machine-readable form, so that the information on the tag may easily be read-in and entered into the report form by means of a suitable scanner or reader. Preferably, the tag should include a read-write memory such an RFID chip for encoding the information. Then, one and the same tag may be used for recording different kinds of treatment (and possibly the animal identifier), so that each animal would have to bear only a single tag. In this case, the step of marking or tagging an animal on the occasion of the a specific treatment act may simply consist of writing new information into a tag that had been applied earlier.

In the cases where tagging includes the application of a physical tag to the animal, the method according to the invention may also comprise a preparatory step of online ordering of the tags. In this case, it is preferable that the tag identifiers are also administrated online.

It will also be useful if the electronic report form and the software program include fields and operations for automating or at least assisting in accounting procedures of the veterinarian. Various types of electronic signature may be used by the veterinarian or witnesses for certifying the report.

The invention also pertains to a software product (e.g. a tangible carrier such as a floppy disk, USB-stick or DVD, or an intangible product downloadable from a server) including program code that enables defining an electronic report form suitable for use in the method as defined here-above, and further including a software program that, when started on a computer in this method, causes the computer to automatically send data that have been entered into the report form to the plurality of remote databases via the network and causes the data to be entered into the databases and further causes the writer to write the copy of the report, which copy is a certificate that proves sending of the data to the databases.

BRIEF DESCRIPTION OF THE DRAWINGS

Embodiments of the invention will now be described in conjunction with the drawings, wherein:

FIG. 3 shows a layout of an electronic report form.

DETAILED DESCRIPTION

Figure 1:
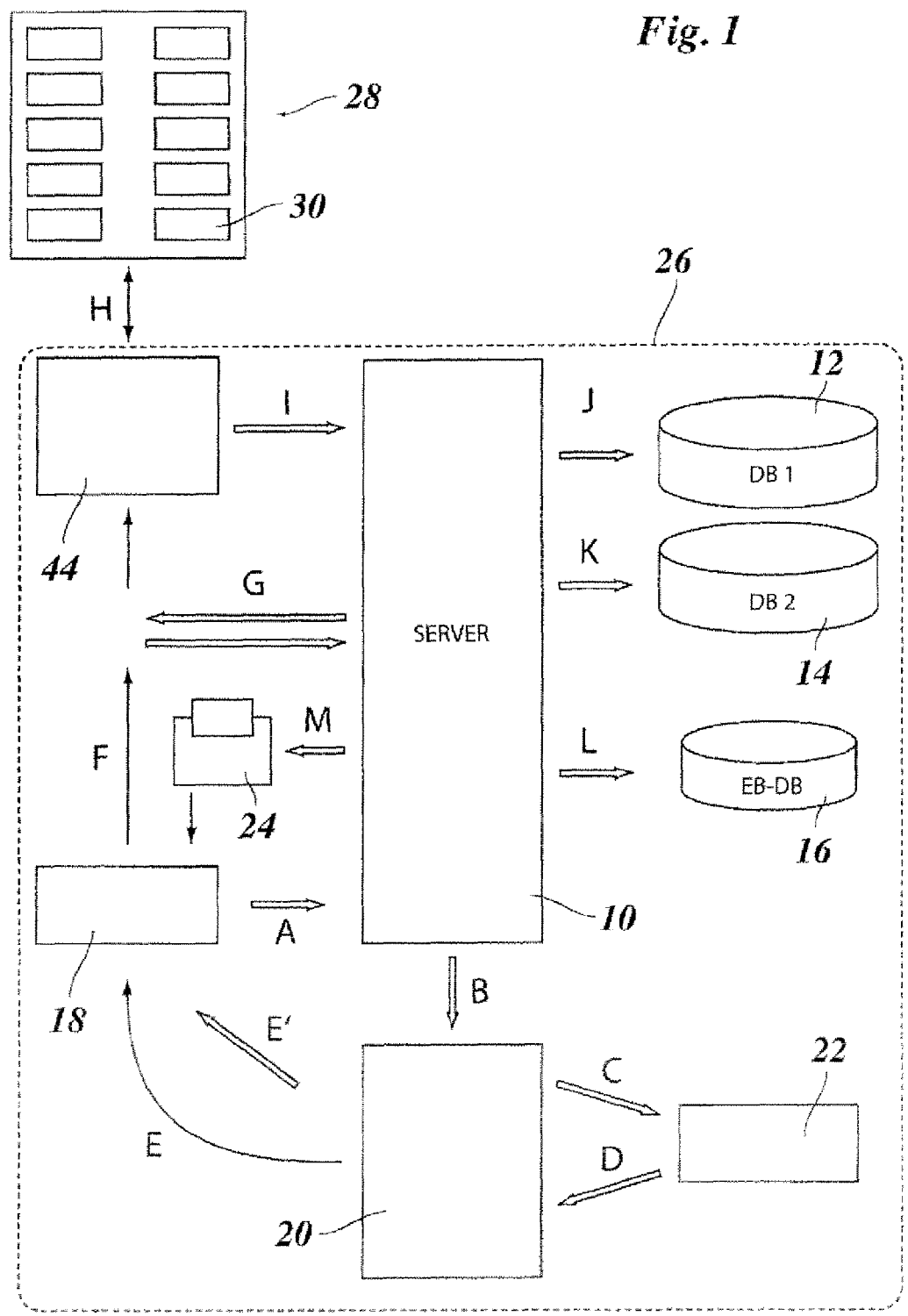
FIG. 1 is a block diagram illustrating essential steps of the method according to the invention.

As is shown in FIG. 1, a server 10, a number of databases 12, 14, 16, terminal devices of a veterinarian 18, a tag manufacturer 20 and a tag administration authority 22, and a printer 24 are interconnected by a network 26 such as the Internet. Network connections among the various entities are also symbolized by arrows that have been shown in contour lines. The database 12 (DB1) may for example be a database that is run by a federal authority for recording and monitoring vaccination of animals against a Governmentally Regulated Disease, e.g. the vaccination of cattle against brucellosis.

The database 14 (DB2) may be a database that serves essentially for the same purpose but is run by a state authority, a supranational authority or the like. The database 16 (EB-DB) is an event based database, e.g. an animal tracking database that is run by a governmental authority or a commercial organization within the framework of NAIS. The database 16 may also be run by one of the authorities that run the databases 12 and 14.

FIG. 1 further shows premises of a breeder 28 who owns a heard of animals 30 (e.g. cattle) that need to be treated (vaccinated).

The veterinarian (vet) 18 is accredited for executing this treatment. He will therefore visit the breeder 28 to vaccinate the animals 30. The veterinarian is also obliged to mark the animals that have been vaccinated with a specific mark, e.g. an ear tag, to certify for each individual animal 30 that it has been vaccinated and to report this to at feast the authorities that run the databases 12 and 14.

In order to fulfill this job, the vet 18 will at first connect to the server 10 and order a sufficient supply of tags (arrow A). The server 10 will forward this order to the tag manufacturer 20 (arrow B) who will in turn ask the administration authority 22 to assign a suitable number of unique identifiers (numbers) for the tags that have been ordered by the vet (arrow C). In response, the authority 22 will notify these identifiers to the manufacturer 20 (arrow D) who will then manufacturer the tags and encode the respective identifiers thereon, e.g. by punching the number into the surface of the tag material. The manufacturer 20 will package the tags and will ship them to the vet 18 (arrow E).

Optionally, the manufacturer 20 may send an online message (arrow E') to the vet 18, preferably via the server 10, notifying the tag identifiers, the date of shipment and the like.

Figure 2:
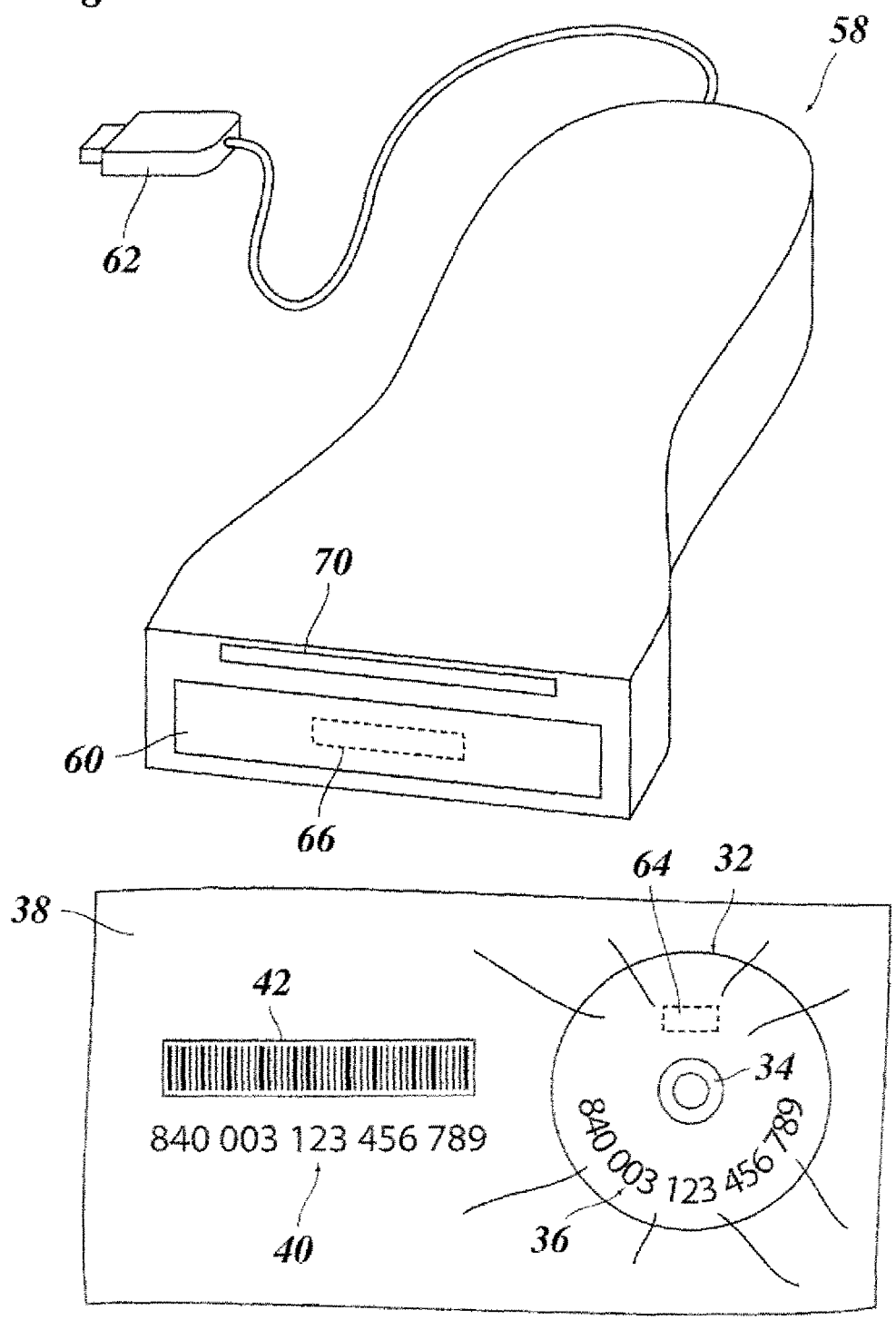
FIG. 2 is a schematic view of a reading device and a tag package that are used in the method according to the invention.

By way of example, FIG. 2 shows a tag 32 as packaged and shipped by the manufacturer 20. The tag 32 has the form of a plastic disk equipped with a fastener 34 for being permanently fastened to the ear of the animal. The color of the tag 32 encodes the type of disease against which vaccination is administered. An identifier 36, i.e. a number, that is unique for the tag and has been assigned by the administration authority 22 is punched into the surface of the tag.

Each individual tag 32 is packaged in a blister package 38 that bears the same identifier as the tag in the form of a man-readable number 40 and also in the form of the machine-readable code 42, e.g. a bar code.

When the vet 18 has received his supply of tags, he connects to the server 10 to download (arrow G) an electronic report form 44 onto his terminal device which will preferably be a mobile device such as a notebook computer, a PDA or the like. Equipped with his supplies of tags and vaccine and his mobile device, the vet 18 visits the breeder 28 (arrow F) where he will vaccine the animals 30 and fill-in the electronic report form 44 (double-arrow H).

As an alternative, instead of downloading the report form onto his own mobile device, the vet may use a terminal device of the breeder 28 in order to connect to the server 10 and to download the report form 40. In that case, the vet may identify and authenticate himself to the server 10 by a password, an electronic signature or the like.

Figure 3:
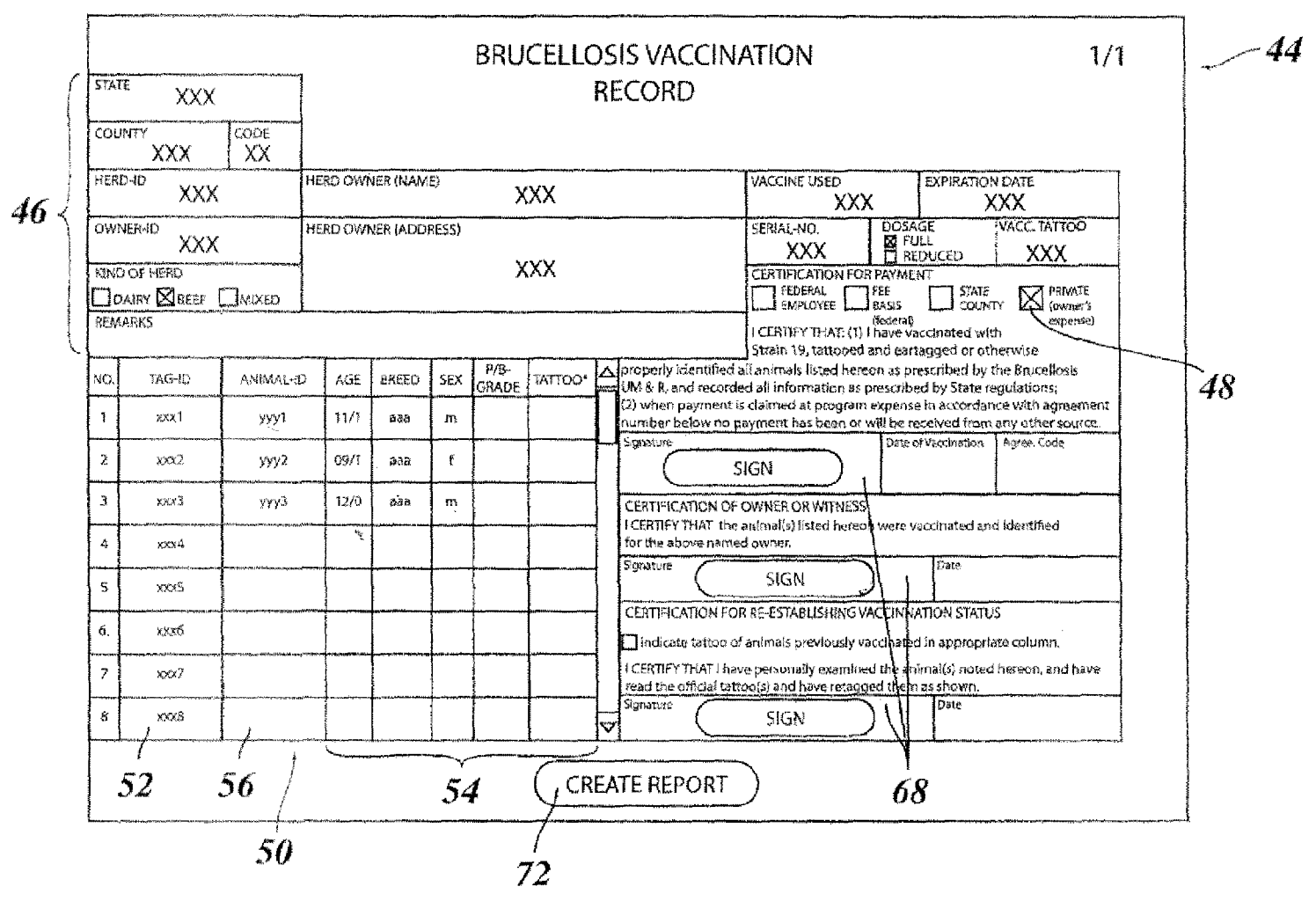

FIG. 3 shows an example of a possible layout of the electronic report form 44. This layout is quite similar to the layout of conventional paper based report form sheets, in this case for brucellosis vaccination.

The layout includes a number of header fields 46 identifying the pertinent authority/authorities to which to report, the herd owner (breeder), the herd to be vaccinated, the vaccine and the like. These fields may be completed by the vet in advance, when he decides to visit the specific breeder 28.

In a modified embodiment, the vet may also use the network 26 and the server 10 for online ordering of the vaccine. In that case, the identification of the vaccine, including a serial number and the expiration date, may be provided online by the vaccine supplier and may automatically be inserted into the report form upon a command entered by the vet. The header of the form further includes a member of check boxes 48 that may be used for automatic (online) accounting for the services of the vet.

The body part of the form 44 includes a list 50 of the animals 30 that are being vaccinated and tagged. Each row in the list 50 is assigned to an individual animal 30, and the list is scrollable, so that the number of rows may always be as large as needed.

A column 52 of the list 50 indicates the tag IDs 36 with which the respective animals have been tagged. Other columns 54 are used for describing the animals as by age, sex and the like. One of these columns may indicate whether or not an animal bears already a tag or a tattoo that refers to an earlier vaccination.

In the example shown, a specific column 56 of the list 50 is provided for entering an animal ID of the animal that has been treated. In a modified embodiment, however, the tag ID indicated in column 52 may used as the animal ID, and the column 56 may be omitted.

There are various ways how the fields of the list 50 can be filled-in. In a most straightforward manner, the vet may simply type-in the required information on his own or the breeder's terminal device.

In case that the vet has received the tag IDs online (arrow E' in FIG. 1), these tag IDs may have been inserted automatically in column 52, and the vet only needs to type-in the animal description and the animal ID, as the case may be. Then, when the list 50 is closed (by a procedure that will be described later) only the rows and the tag IDs for which animal descriptions have been entered will remain in the list, and the excess tag IDs will be removed from the list and will be saved until the vet visits the next breeder.

In another embodiment that has been illustrated in FIG. 2, the vet uses a hand-held reading device 58 that includes a bar code reader 60 for reading the code 42 from the packages 38 of the tags, e.g. immediately before the package is opened and the tag 32 is applied to the animal. The device 58 includes an electronic memory and a USB interface 62 which may be plugged into the mobile device of the vet or the breeder, so that the scanned IDs may be copied into the list 50.

Of course, the bar code reader 60 may be replaced by any other suitable device such as a camera and OCR software for reading written text, a microphone and a speech recognition software for oral data input, and the like. In the latter case, the speech recognition software may also be used for completing the other fields of the form 44, especially the animal description fields, the animal identifier and the like.

On the other hand, if the bar code reader 60 is used, it may be convenient that the animal descriptions are encoded as bar code (or other machine readable code) right at the booth of the respective animal 30, so that the animal IDs and animal descriptions may also be read-in automatically. In yet another embodiment, these data may be imported from a private database of the breeder.

In place of the USB interface 62, the reading device 58 may be equipped with a bluetooth interface or any other suitable device for wireless communication with the terminal device of the vet or the breeder.

In yet another embodiment which has been illustrated in FIG. 2 in phantom lines and which is at present considered to be the preferred embodiment, the tag 32 includes an electronic memory 64, preferably a read-write memory such as an RFC chip, and the reading device 58 includes a transceiver 66 for wireless communication with the memory 64. Thus, the tag ID 36 may also be stored in the memory 64 and may be read with the transceiver 66 so has to be entered into the list 50. Conversely, the transceiver 66 may be used for writing an animal ID or possibly the complete animal description and also information on the present treatment (e.g. the kind of vaccination and the vaccination date) into the memory 64.

When this embodiment of the method according to the invention is employed for several diseases, it will be sufficient to provide only a single tag 32 for each animal, and information on different treatments (vaccinations against different diseases) may be stored on the memory 64 and may be read therefrom as desired. Then, in order for the authorities to be able to keep track of the individual vaccination events, in case that a tag had already been applied to the animals in conjunction with an earlier treatment, the procedure that has been illustrated by arrows A-E in FIG. 1 may be replaced by a different procedure, According to this procedure, the vet 18 will directly ask the administration authority 22 to assign IDs for "virtual tags", and the authority 22 will respond by sending these IDs directly to the vet. Then, when the vet visits the breeder 28 and vaccinates the animals, he will write these tag IDs into the memories 64 on the already existing tags and will insert the same tag IDs in column 52 of the list 50 (FIG. 3).

As conventional forms on paper, the electronic report form 64 shown in FIG. 3 has signature fields 68 permitting the vet to certify that he has actually vaccinated (or otherwise treated) the animals, and permitting the owner or another witness to confirm this fact. Another signature field is used for certifying that an animal that had already a tattoo has be retagged.

Since the form 44 is an electronic form, the hand-written signature has to be replaced by any other suitable signing mechanism that can assure the identity of the person signing. For example, passwords, PIN codes and the like may be used to that end. In the example shown in FIG. 2, the reading device 58 has an integrated card reader 70 for reading personalized signature cards of the vet and/or the breeder. The signature fields 68 in FIG. 3 include "SIGN" buttons that will be active only on condition that the pertinent signature card has been entered. Once the card owner has clicked onto the sign button, identification information from the signature card will be stored in the electronic form, the name of the person signing will appear in the signature field, and the date of signature and, in case of the vet 18, the accreditation code will automatically be added.

If the reading device 58 has no card reader 70, any standalone standard card reader may be used.

Instead of using signature cards, the identity of the persons signing may also be assured be providing these persons with identity cards bearing an identity code in machine readable form that may be read with the bar code reader 60, for example.

When the report form 44 (FIG. 3) has been completed, the user (the vet) clicks a button 72 "CREATE REPORT" 72. This will call-up a software program that executes a number of actions that are inseparably linked to one another. First, the software will perform a number of checks to see whether the data entries in the form comply with the standard formats and are consistent with one another. If not, an error message will prompt the user to correct the entries. Then, the list 50 will be closed and the data entered into the form 44 will be saved. Thereafter, the contents of the report form 44 or at least the contents of specified fields thereof are automatically transmitted via the network 26 to the databases 12, 14 and 16 that have to that end been specified in the software program (arrows I, J, K and L in FIG. 1). In the databases 12-16, the pertinent information will automatically be entered into the database fields that have been provided therefor. Thus, it is assured that all databases are always kept updated with identical or at least consistent information. Further, the printer 24 is activated (arrow M) to print one or more hard copies of the report to be handed out the reader and/or be kept in the files of the vet.

In the example shown in FIG. 3, the report consists of only one page as is indicated by a page number "1/1". If the number of animals is larger than 8, so that they can not all been shown simultaneously in the scrollable list 50, the list is divided onto several pages, and the printed report will consist of a corresponding number of pages each of which bears the page number and the total numbers of pages of the report.

The software program that enforces all the actions indicated above may permanently reside on terminal device of the vet 18 or may be downloaded from the server 10 together with the report form 44. In yet another embodiment, the software program may reside on the server 10. In that case, the button 72 has just the function to transmit the completed form 44 to the server 10 and to activate the software program there.

What is claimed is:

1. A method of documenting an animal treatment, comprising the steps of:
   downloading an electronic report form from a server via a network;
   entering a plurality of data regarding the treatment into the report form when the animal is treated, wherein said plurality of data includes an identification of the type of treatment and at least a unique identifier of the treatment act;
   starting a software program that specifies a plurality of remote databases, further specifies a plurality of fields in the report form for which corresponding fields are provided in said specified databases, and automatically sends said plurality of data that has been entered into the specified plurality of fields of the report form to a plurality of said remote databases via the network;
   wherein the specified plurality of fields of the report form may be arranged in a different order than that of said corresponding fields in any of said specified databases;
   wherein said starting of the software program causes said plurality of data to be entered into the databases and further causes a writer to write a copy of the report; and
   wherein said copy is a certificate that proves the sending of said plurality of data to the databases.

2. The method according to claim 1, wherein said plurality of remote databases includes at least one event based database.

3. The method according to claim 1, wherein the animal treatment to be documented is a vaccination treatment.

4. The method according to claim 3, further comprising a step of online ordering a vaccine.

5. The method according to claim 1, further comprising a step of certifying the report by a person.

6. The method according to claim 5, wherein an identity of the person that certified the report is provided, thereby allowing the identity to be checked.

7. The method according to claim 1, further comprising a step of marking the treated animal with a physical mark that has encoded therein at least said unique identifier.

8. The method according to claim 7, wherein said physical mark is a tag that includes a machine-readable memory.

9. The method according to claim 8, wherein said memory is a read-write memory and said marking step includes a step of writing data into the memory.

10. The method according to claim 9, wherein said physical mark has encoded therein a unique identifier of the animal, and a single tag per animal is used for documenting different kinds of treatment.

11. The method according claim 7, comprising a step of ordering the marks online.

12. The method according to claim 1, wherein an electronic reading device is used for reading data into the electronic report form.

13. The method according to claim 1, wherein said software program performs a step of checking the data that have been entered into the report form for errors and/or inconsistencies before sending the data to the remote databases.

14. The method according to claim 1, wherein said software program performs an accounting step on the basis of data entered into the report form.

15. A software product embodied on a memory device including program code that enables defining an electronic report form suitable for use in a method of documenting an animal treatment, which further includes a software program that when started on a computer in said method, causes the computer to specify a plurality of remote databases, further to specify a plurality of fields in the report form for which corresponding fields are provided in said specified databases, and to automatically send a plurality of data that have been entered into the report form to the plurality of remote databases via the network and causes the said plurality of data to be entered into the specified plurality of fields of the plurality of remote databases and further causes the writer to write the copy of the report; wherein said copy is a certificate that proves the sending of said plurality of data to the plurality of remote databases;

wherein said method of documenting an animal treatment comprises:

downloading an electronic report form from a server via a network;

entering a plurality of data regarding the treatment into the report form when the animal is treated, wherein said plurality of data includes an identification of the type of treatment and at least a unique identifier of the treatment act; and starting a software program that specifies a plurality of remote databases, further specifies the plurality of fields in the report form for which corresponding fields are provided in said specified databases, and automatically sends said plurality of data that has been entered into the specified plurality of fields of the report form to a plurality of said remote databases via the network;

wherein the specified plurality of fields of the report form may be arranged in a different order than that of said corresponding fields in any of said specified databases;

wherein said starting of the software program causes said plurality of data to be entered into the databases and further causes a writer to write a copy of the report; and wherein said copy is a certificate that proves the sending of said plurality of data to the databases.

* * * * *